(12) United States Patent
Broyles et al.

(10) Patent No.: US 10,800,140 B2
(45) Date of Patent: *Oct. 13, 2020

(54) MULTI-LAYERED THERMOPLASTIC POLYMER FILMS COMPRISING POLYLACTIC ACID

(71) Applicant: The Procter & Gamble Company, Cincinnati, OH (US)

(72) Inventors: Norman Scott Broyles, Hamilton, OH (US); April Renae Brown, Cincinnati, OH (US); Gary Wayne Gilbertson, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/232,141

(22) Filed: Dec. 26, 2018

(65) Prior Publication Data

US 2019/0143643 A1 May 16, 2019

Related U.S. Application Data

(63) Continuation of application No. 14/726,645, filed on Jun. 1, 2015, now Pat. No. 10,259,195.

(51) Int. Cl.
*B32B 7/12* (2006.01)
*A61L 15/24* (2006.01)
(Continued)

(52) U.S. Cl.
CPC .......... *B32B 7/12* (2013.01); *A61F 13/51401* (2013.01); *A61L 15/24* (2013.01);
(Continued)

(58) Field of Classification Search
CPC ............ B32B 2250/03; B32B 2250/04; B32B 2250/05; B32B 2250/24; B32B 2270/00;
(Continued)

(56) References Cited

U.S. PATENT DOCUMENTS

| 5,910,545 A | 6/1999 | Tsai et al. |
| 6,177,193 B1 | 1/2001 | Tsai et al. |

(Continued)

FOREIGN PATENT DOCUMENTS

| EP | 2297385 B1 | 12/2012 |
| JP | 2008044365 | 2/2008 |

(Continued)

OTHER PUBLICATIONS

13393M Search Report and Written Opinion for PCT/US2015/033452 dated Jul. 16, 2015.
13393M All Office Actions for U.S. Appl. No. 14/726,645.

*Primary Examiner* — Lawrence D Ferguson
(74) *Attorney, Agent, or Firm* — Daniel S. Albrecht

(57) ABSTRACT

A multi-layered film comprising at least 3 layers is provided. When a 5 layered film is provided, the film includes a first outer layer having 80% to 100% by weight of one or more polyolefins, a first tie layer having from 5% to 100% by weight of the first tie layer of one or more functionalized polyolefins, a core layer having from 75% to 100% by weight of the core layer of polylactic acid, a second tie layer having from 5% to 100% by weight of second tie layer of one or more functionalized polyolefins, and a second outer layer having from 80% to 100% by weight of the second outer layer of one or more polyolefins, wherein the first tie layer layer is disposed between the first outer layer and the core layer the second tie layer is disposed between the core layer and the second outer layer.

20 Claims, 1 Drawing Sheet

Related U.S. Application Data

(60) Provisional application No. 62/006,508, filed on Jun. 2, 2014.

(51) Int. Cl.
*A61L 15/26* (2006.01)
*A61F 13/514* (2006.01)
*B32B 27/08* (2006.01)
*B32B 27/32* (2006.01)
*B32B 27/36* (2006.01)

(52) U.S. Cl.
CPC .............. *A61L 15/26* (2013.01); *B32B 27/08* (2013.01); *B32B 27/32* (2013.01); *B32B 27/36* (2013.01); *B32B 2250/03* (2013.01); *B32B 2250/04* (2013.01); *B32B 2250/05* (2013.01); *B32B 2250/24* (2013.01); *B32B 2270/00* (2013.01); *B32B 2307/54* (2013.01); *B32B 2307/726* (2013.01); *B32B 2307/7265* (2013.01); *B32B 2432/00* (2013.01); *B32B 2555/00* (2013.01); *B32B 2555/02* (2013.01); *Y10T 428/269* (2015.01)

(58) Field of Classification Search
CPC .......... B32B 2307/54; B32B 2307/726; B32B 2307/7265; B32B 2432/00; B32B 2555/00; B32B 2555/02; B32B 27/08; B32B 27/32; B32B 27/36; B32B 7/12; Y10T 428/269

See application file for complete search history.

(56) References Cited

U.S. PATENT DOCUMENTS

| | | | |
|---|---|---|---|
| 6,309,988 B1 | 10/2001 | Tsai et al. |
| 6,506,873 B1 | 1/2003 | Ryan et al. |
| 7,132,490 B2 | 11/2006 | Obuchi et al. |
| 7,303,642 B2 | 12/2007 | Topolkaraev |
| 7,744,576 B2 | 6/2010 | Busam et al. |
| 7,951,438 B2 | 5/2011 | Lee et al. |
| 8,137,773 B2 | 3/2012 | Hiruma et al. |
| 8,461,262 B2 | 6/2013 | McEneany et al. |
| 8,507,084 B2 | 8/2013 | Deng |
| 2005/0164587 A1 | 7/2005 | Melik et al. |
| 2007/0275196 A1* | 11/2007 | Opuszko ............ B32B 7/02 428/35.2 |
| 2008/0026171 A1 | 1/2008 | Gullick et al. |
| 2008/0085066 A1 | 4/2008 | Curie |
| 2008/0280117 A1 | 11/2008 | Knoll |
| 2009/0263600 A1 | 10/2009 | Miyashita et al. |
| 2009/0324911 A1 | 12/2009 | Li et al. |
| 2009/0326152 A1 | 12/2009 | Li et al. |
| 2011/0052867 A1 | 3/2011 | Yamamura et al. |
| 2012/0009387 A1 | 1/2012 | Wang |
| 2012/0022188 A1 | 1/2012 | Changping et al. |
| 2012/0035323 A1 | 2/2012 | Donnelly |
| 2012/0219783 A1 | 8/2012 | Nomura et al. |
| 2013/0004760 A1 | 1/2013 | Pellingra |
| 2013/0157032 A1 | 6/2013 | Wang et al. |
| 2013/0190408 A1 | 7/2013 | Scholz et al. |
| 2013/0211356 A1 | 8/2013 | Nishikawa et al. |
| 2013/0333787 A1 | 12/2013 | Shi et al. |
| 2014/0031436 A1 | 1/2014 | Hamann et al. |
| 2014/0127460 A1 | 5/2014 | Xu et al. |
| 2015/0343748 A1 | 12/2015 | Broyles et al. |

FOREIGN PATENT DOCUMENTS

| | | |
|---|---|---|
| JP | 4167107 | 10/2008 |
| JP | 4390798 | 12/2009 |
| JP | 2010173114 | 8/2010 |
| WO | WO2008023721 | 2/2008 |

* cited by examiner

MULTI-LAYERED THERMOPLASTIC POLYMER FILMS COMPRISING POLYLACTIC ACID

CROSS REFERENCE TO RELATED APPLICATIONS

This application is a continuation of, and claims priority under 35 U.S.C. § 120 to, U.S. patent application Ser. No. 14/726,645, filed on Jun. 1, 2015, which claims the benefit, under 35 U.S.C. § 119(e), to U.S. Provisional Patent Application Ser. No. 62/006,508, filed on Jun. 2, 2014, the entire disclosures of which are hereby fully incorporated by reference herein.

FIELD OF THE INVENTION

The present invention generally relates to multi-layered thermoplastic polymer films comprising polylactic acid.

BACKGROUND OF THE INVENTION

Many products today utilize films. Some examples of such products include, but are not limited to, personal care absorbent products such as diapers, training pants, incontinence garments, sanitary napkins, bandages, wipes and the like, as well as products such as packaging materials, and other disposable products such as trash bags and food bags. These films are typically made from thermoplastic polymers.

Many thermoplastic polymers are derived from monomers that are obtained from non-renewable, fossil-based resources such as petroleum, natural gas, and coal. In recent years, as manufacturers and consumers have gained a greater awareness of environmental and sustainability concerns, the demand for polymers made from renewable, non-fossil-based materials has grown significantly. Unfortunately, however, many renewable thermoplastic biopolymers are not well suited for solo use in stand-alone applications. Associated with the desire to reduce utilization of non-renewable natural resources, the ability to "down-gauge" or reduce the thickness and/or polymer content of films, products and packages while maintaining performance is also advantageous. Technologies that reduce the utilization of non-renewable natural resources through incorporation of biopolymers while also enabling down gauging are highly desired.

Attempts have been made in the art at producing films, fibers and other compositions from renewable biopolymers, such as polylactic acid (see, e.g., EP 2285892; WO 2008/149943; U.S. Pat. Nos. 5,910,545; 6,177,193; 6,309,988; 6,506,873; 7,132,490; 8,137,773; 8,461,262; 2009/0263600; 2009/0326152; 2009/0324911; 2012/0035323; 2012/0219783; 2013/0157032 and 2013/0190408). However, the use of PLA may result in deficiencies in the context of making thin, flexible packaging films such as those typically used for personal hygiene articles, wipes, product bags, and for personal care products. For instance, PLA thin film exhibits high stiffness, brittleness, high rustling noise levels when handled, low extensibility, low ductility, and low toughness relative to polyolefin. As such, PLA is not typically used as a major component in films for such applications.

Thermoplastic polymers such as polyolefins ("PO") are commonly used to produce thin films for consumer product packaging because of their excellent processability. As a result, common film-manufacturing equipment is optimally designed for making polyolefin-based films. Replacing or modifying this manufacturing equipment to run other types of polymers would require high development costs and excessive capital expenditures, making this option impractical for most manufacturers.

Accordingly, thermoplastic polymer compositions that are not only suitable for making thin films using standard polyolefin film-manufacturing equipment, but also contain bio-based content having good mechanical properties, are highly desirable.

SUMMARY OF THE INVENTION

A multi-layered film comprising at least 3, preferably at least 5, layers is provided. In the case of a 5 layered film, the multi-layer film includes a first outer layer having 80% to 100% by weight of one or more polyolefins, a first tie layer having from 5% to 100% by weight of the first tie layer of one or more functionalized polyolefins, a core layer having from 75% to 100% by weight of the core layer of polylactic acid, a second tie layer having from 5% to 100% by weight of second tie layer of one or more functionalized polyolefins, and a second outer layer having from 80% to 100% by weight of the second outer layer of one or more polyolefins, and wherein the first tie layer layer is disposed between the first outer layer and the core layer the second tie layer is disposed between the core layer and the second outer layer.

BRIEF DESCRIPTION OF THE DRAWINGS

FIGURE is a cross-sectional view of one example of a multi-layer film described herein.

DETAILED DESCRIPTION

I. Definitions

As used herein, the following terms shall have the meanings specified thereafter: "Absorbent article" refers to any absorbent consumer product or portion thereof, including absorbent personal hygiene articles (e.g., wipes, diapers, diaper components such as a backsheets or portion of a backsheet, training pants, absorbent underpants, adult incontinence products, feminine hygiene products such as pads and tampons; coverings (e.g., floor coverings, table cloths, picnic area covers); medical products (e.g., surgical gowns and drapes, face masks, head coverings, shoe coverings, wound dressings, bandages, sterilization wraps, and the like for medical, dental or veterinary applications); and garments (any type of apparel which may be worn, e.g., industrial work wear and coveralls, undergarments, pants, shirts, jackets, gloves, socks, head coverings, shoe coverings, aprons, surgical clothing, and the like).

"Bio-polymers" refers to polymers derived from biological materials, typically plant materials.

"Copolymer" refers to a polymer derived from two or more polymerizable monomers. When used in generic terms the term "copolymer" is also inclusive of more than two distinct monomers, for example, ter-polymers. The term "copolymer" is also inclusive of random copolymers, block copolymers, and graft copolymers.

"Contiguous" means in direct contact with. Where a layer is "contiguous," it is in direct contact with at least one adjacent layer.

"Cross machine direction" or "CD" refers to the width of film, i.e. a direction generally perpendicular to the MD.

"Film" refers to a sheet-like material wherein the length and width of the material far exceed the thickness of the material. As used herein, the terms "film" and "sheet" are used interchangeably.

"Joined to" encompasses configurations in which an element is directly secured to another element by affixing the element directly to the other element, and configurations in which the element is indirectly secured to the other element by affixing the element to intermediate member(s) which in turn are affixed to the other element.

"Machine direction" or MD means the length of film as it is produced.

"Renewable" refers to a material that can be produced or is derivable from a natural source which is periodically (e.g., annually or perennially) replenished through the actions of plants of terrestrial, aquatic or oceanic ecosystems (e.g., agricultural crops, edible and non-edible grasses, forest products, seaweed, or algae), or microorganisms (e.g., bacteria, fungi, or yeast).

"Substantially no", "substantially free of", and/or "substantially free from" mean that the indicated material is at the very minimum not deliberately added to the composition to form part of it, or, most desirably, is not present at analytically detectable levels. It is meant to include compositions whereby the indicated material is present only as an impurity in one of the other materials deliberately included. In some embodiments, substantially free of means that the layer or film comprises less than 5%, 3%, 2%, 1%, 0.5%, 0.1% or 0.01% by weight of the ingredient or material.

As used herein, articles such as "a" and "an" are understood to mean one or more of what is claimed or described.

As used herein, the terms "include", "contain", and "has", as well as their various verb tenses, are meant to be non-limiting.

All percentages and ratios are calculated by weight of the total composition, unless otherwise indicated.

Unless otherwise noted, all component or composition levels are in reference to the active portion of that component or composition, and are exclusive of impurities, for example, residual solvents or by-products, which may be present in commercially available sources of such components or compositions.

The multi-layer films described herein comprise at least 3, preferably 4, and more preferably at least 5 layers. One example of a 5 layer multi-layer film 10 is shown in FIG. 1, wherein the multi-layer film 10 comprises two or more outer or skin layers 15, two or more tie layers 20, and one or more core layers 25. The multi-layer films may have an average thickness from about 5, 10, 15, 20, to about 25, 30, 40, 50, 60, 70, 80, 90 or 100 microns. Similar layers need not be the same compositionally, structurally or geometrically. For example, the tie layers 20 may be the same, substantially the same, or compositionally, structurally, or geometrically dissimilar. Similarly, outer layers 15 may be the same, substantially the same, or compositionally, structurally or geometrically dissimilar. For example, outer layers 20 may be compositionally different from each other if different heat sealing properties are desired between the two outer layers.

II. Outer Layers Comprising Thermoplastic Polymer(S)

The outer or skin layers of the multi-layer film each comprise one or more thermoplastic polymers, preferably one or more polyolefins. In some embodiments, the skin layer comprises from 75%, 80%, 85% or 90% to 95% or 100% by weight of the skin layer of the one or more polyolefins with the balance comprising other thermoplastic polymers or additives. In some embodiments, the outer or skin layers are substantially or completely free of polylactic acid. Thermoplastic polymers, as used herein, are polymers that melt and then, upon cooling, crystallize or harden, but can be re-melted upon further heating. Suitable thermoplastic polymers for use herein typically have a melting temperature from 60° C. to 300° C., from 80° C. to 250° C., or from 100° C. to 215° C. The molecular weight of the thermoplastic polymer is sufficiently high to enable entanglement between polymer molecules and yet low enough to be melt extrudable. Suitable thermoplastic polymers can have weight average molecular weights of 1000 kDa or less, 5 kDa to 800 kDa, 10 kDa to 700 kDa, or 20 kDa to 400 kDa. The weight average molecular weight is determined by the specific ASTM method for each polymer, but is generally measured using either gel permeation chromatography (GPC) or from solution viscosity measurements.

Polyolefins are produced from olefin (alkene) monomers, either a single olefin species or a combination of two or more olefin species. Common polyolefins include polyethylene ("PE"), polypropylene ("PP"), polymethylpentene ("PMP"), polybutene-1 ("PB-1"), low density polyethylene ("LDPE"), high density polyethylene ("HDPE"), linear low density polyethylene ("LLDPE"), polyisobutene ("PIB"), cross-linked polyethylene (XLPE), crosslinked high density polyethylene (PEX), and copolymers thereof.

As used herein, the generic term "polyolefin" includes both non-functionalized polyolefins and functionalized polyolefins. Non-functionalized polyolefins are those consisting essentially of olefin species, while functionalized polyolefins are those containing one or more chemical functional groups. Non-functionalized polyolefins are very chemically inert and have excellent chemical resistance, low surface energies, and low wetting ability, making them ideal for some applications but not for others. In order to improve wetting, mix dispersion, filler adhesion, melt processing, surface-to-surface attraction and/or other desired performance features, polyolefins can be chemically modified ("functionalized") with functional groups to impart the desired properties to the polyolefin polymer. As disclosed in the art, approaches to polyolefin functionalization can include those such as: (1) direct copolymerization of α-olefin with functional monomer, (2) chemical modification of the preformed polymer, and (3) a reactive copolymer approach, incorporating reactive co-monomers that can be selectively and effectively interconverted to functional groups.

Polyolefins typically used herein include polyethylene or copolymers thereof, including low density, high density, linear low density, or ultra low density polyethylenes such that the polyethylene density ranges from 0.85 grams per cubic centimeter to 0.97 grams per cubic centimeter, or from 0.92 to 0.95 grams per cubic centimeter. The density of the polyethylene is determined by the amount and type of branching and depends on the polymerization technology and co-monomer type.

Polypropylene and/or polypropylene copolymers, including atactic polypropylene, isotactic polypropylene, syndiotactic polypropylene, or combinations thereof can also be used. Polypropylene copolymers, especially ethylene, can be used to lower the melting temperature and improve properties. These polypropylene polymers can be produced using metallocene and Ziegler-Natta catalyst systems. These polypropylene and polyethylene compositions can be combined together to custom engineer end-use properties.

If the polyolefin comprises polyethylene, some non-limiting examples of suitable polyethylenes include very low density polyethylene (VLDPE) or ultra low density polyethylene (ULDPE), low density polyethylene (LDPE), linear low density polyethylene (LLDPE) which may, have a density ranging from 0.915 g/cm$^3$ to 0.925 g/cm$^3$, linear medium density polyethylene (LMDPE) or medium density polyethylene (MDPE) which may have a density ranging from 0.926 g/cm$^3$ to 0.94 g/cm$^3$, and/or high density polyethylene (HDPE) which may have a density of greater or equal to 0.941 g/cm$^3$ up to 0.97 g/cm$^3$ or more, and blends thereof. Suitable grades of LUPE include, but are not limited to, those having a melt index at 190° C. of about 0.2 g/10 min to about 7 g/10 min at a load of 2.16 kg. In some embodiments, the continuous phase of the soft touch film composition comprises a combination of LLDPE and LDPE or MDPE, some examples of which are available from Baskem as SLH218 (LLDPE), from Exxon Mobil (LDPE), from the Dow Chemical Co. as DOWLEX™ 2045 (oLLDPE) and from the Dow Chemical Co. as DOWLEX$^{IM}$ 2027 (LMDPE). Reference herein to a density or melt index of a polyethylene polymer is intended to mean a density or melt index determined in accordance with ASTM D792 and ASTM D 1238, respectively.

If the polymer is polypropylene, the polyolefin can have a melt flow index (MFI) of greater than 0.1 g/10 min, as measured by ASTM D-1238, used for measuring polypropylene. Other contemplated melt flow indices include greater than 1 g/10 min, greater than 10 g/10 min.

Non-limiting examples of suitable commercially available polypropylene or polypropylene copolymers include Basell ProfaxPH835™ (a 35 melt flow rate Ziegler-Natta isotactic polypropylene from Lyondell-Basell), Basell Metocene MF-650 W™ (a 500 melt flow rate metallocene isotactic polypropylene from Lyondell-Basell), Polybond3200™ (a 250 melt flow rate maleic anhydride polypropylene copolymer from Crompton), Exxon Achieve3854™ (a 25 melt flow rate metallocene isotactic polypropylene from Exxon-Mobil Chemical), and Mosten NB425™ (a 25 melt flow rate Ziegler-Natta isotactic polypropylene from Unipetrol). Other suitable polymers may include; Danimer 27510™ (a polyhydroxyalkanoate polypropylene from Danimer Scientific LLC), Dow Aspun 6811 A™ (a 27 melt index polyethylene polypropylene copolymer from Dow Chemical), and Eastman 9921™ (a polyester terephthalic homopolymer with a nominally 0.81 intrinsic viscosity from Eastman Chemical).

In those embodiments where the outer or skin layers comprise a thermoplastic polymer other than a polyolefin, the thermoplastic polymer may be derived from renewable resources or from fossil-based materials. The thermoplastic polymers derived from renewable resources are bio-based, such as bio-produced ethylene and propylene monomers used in the production of polypropylene and polyethylene. Renewable material properties are essentially identical to fossil-based product equivalents, except for the presence of carbon-14 in the bio-based thermoplastic polymer. To determine the level of renewable materials present in an unknown composition (e.g., in a product made by a third party), ASTM D6866 test method B can be used to measure the biobased content by measuring the amount of carbon-14 in the product. Materials that come from biomass (i.e. renewable sources) have a well-characterized amount of carbon-14 present, whereas those from fossil sources do not contain carbon-14. Thus, the carbon-14 present in the product is correlated to its bio-based content.

Renewable and fossil based thermoplastic polymers can also be used in combination. Recycled thermoplastic polymers can also be used, alone or in combination with renewable and/or fossil derived thermoplastic polymers. The recycled thermoplastic polymers can be pre-conditioned to remove any unwanted contaminants prior to compounding or they can be used during the compounding and extrusion process, as well as simply left in the admixture. These contaminants can include trace amounts of other polymers, pulp, pigments, inorganic compounds, organic compounds and other additives typically found in processed polymeric compositions. The contaminants should not negatively impact the final performance properties of the admixture.

Biodegradable thermoplastic polymers also are contemplated for use herein. Biodegradable materials are susceptible to being assimilated by microorganisms, such as molds, fungi, and bacteria when the biodegradable material is buried in the ground or otherwise contacts the microorganisms (including contact under environmental conditions conducive to the growth of the microorganisms). Suitable biodegradable polymers also include those biodegradable materials that are environmentally-degradable using aerobic or anaerobic digestion procedures, or by virtue of being exposed to environmental elements such as sunlight, rain, moisture, wind, temperature, and the like. The biodegradable thermoplastic polymers can be used individually or as a combination of biodegradable or non-biodegradable polymers. Biodegradable polymers include polyesters containing aliphatic components.

Suitable thermoplastic polymers generally include thermoplastic starch, polyolefins, polyesters, polyamides, copolymers thereof, and combinations thereof. For example, the thermoplastic polymer can be selected from the group consisting of TPS, polypropylene, polyethylene, polypropylene co-polymer, polyethylene co-polymer, polyethylene terephthalate, polybutylene terephthalate, polylactic acid ("PLA"), polyhydroxyalkanoates ("PHA"), polyamide-6, polyamide-6,6, and combinations thereof.

Other non-limiting examples of suitable polymers include polycarbonates, polyvinyl acetates, poly(oxymethylene), styrene copolymers, polyetherimides, polysulfones, polyvinyl alcohol, ethylene acrylic acid, polyolefin carboxylic acid copolymers, and combinations thereof. Any other suitable thermoplastic polymers, or combinations thereof, may be used herein.

A large number of biodegradable polyesters are based on petroleum resources, obtained chemically from synthetic monomers. These include polycaprolactone, aliphatic copolyesters, and aromatic copolyesters, all of which are soft at room temperature.

Poly(e-caprolactone) (PCL) is usually obtained by ROP of e-caprolactone in the presence of metal alkoxides (e.g., aluminium isopropoxide, tin octoate). PCL is widely used as a PVC solid plasticizer or for polyurethane applications, as polyols. It also finds applications based on its biodegradable character in domains such as biomedicine (e.g. controlled release of drugs) and the environment (e.g. soft compostable packaging). PCL shows a very low Tg (−61° C.) and a low Tm (65° C.), which could be a handicap in some applications. Therefore, PCL is generally blended or modified (e.g., copolymerization, crosslinking). PCL can be hydrolyzed and biodegraded by fungi. PCL can easily be enzymatically degraded.

A large number of aliphatic copolyesters based on petroleum resources are biodegradable copolymers. They are obtained by the combination of diols such as 1,2-ethanediol, 1,3-propanediol or 1,4-butadenediol, and of dicarboxylic acids like adipic, sebacic or succinic acid. Polybutylene succinate (PBS) can be obtained by polycondensation of 1,4-butanediol and succinic acid. Polybutylene succinate/adipate (PBSA) is obtained by addition of adipic acid to 1,4-butanediol and succinic acid polycondensation. Other polycondensation reactions have been used to produce other condensates, such as polycondensation of 1,2-ethanediol, 1,4-butadenediol with succinic and adipic acids to produce aliphatic copolyester. The properties of these copolyesters depend on the structure i.e., the combination of diols and diacids used. The biodegradability of these products depends also on the structure. The addition of adipic acid, which decreases the crystallinity, tends to increase the compost biodegradation rate.

Aromatic copolyesters are often based on terephthalic acid. For instance, the chemical structure of poly(butylene adipate-co-terephthalate) (PBAT).

In certain embodiments, a skin layer or both skin layers may be used as heat seal surfaces. In order to facilitate heat sealing, the skin layer or layers may include heat seal enchancing materials such as low melting polyolfin copolymers such as metalocene plastomers (Exact from ExxonMobil, Affinity from Dow Chemical), polar copolymers such as EVA, EAA, EMA, etc. (Primacor from Dow Chemical), etc.

III. Core Layer Comprising Polylactic Acid

The multi-layer films further comprise one or more core layers that comprise polylactic acid. As used herein, "core layer" refers to a layer that is disposed between the skin layers, but it is not necessary that the core layer be disposed at the geometric middle of the multi-layer film. More preferably, the one or more core layers are disposed between 2 or more tie layers and/or are preferably disposed adjacent to or continuous with the 2 or more tie layers. The core layer preferably comprises from 75%, 80%, 85% or 90% to 95% or 100% by weight of the core layer of polylactic acid. The one or more core layers may consist essentially of polylactic acid. The core layer may have an average thickness from about 0.5, 0.75 1, 1.5, 2, 2.5, 3, 3.5, 4, 4.5, 5, 5.5, 6, 6.5, 7 microns to about 1.5, 2, 2.25, 2.75, 3, 3.25, 3.5, 3.75, 4, 5, 6, 7, 8, 9, 10, 11, 12, 13, 14, 15, 16, 17, 18, 19, 20, 21, 22, 23, 24, 25, 26, 27, 28, 29, 30 microns. The caliper volume fraction of the one or more core layers is preferably less than 30 vol % of the total volume of the multi-layer film in order to minimize the impact that the stiffer PLA material has on bending rigidity of the multi-layer film.

Without intending to be bound by any theory, it is believed that a multi-layer film incorporating one or more core layers comprising 75 wt % or more of PLA, preferably as thin layers, that are disposed between thicker outer or skin layers comprising 80 wt % or more of one or more polyolefins provides a multi-layer film with the MD stiffness advantages of PLA while minimizing the associated effects on bending rigidity. Because the stiffer PLA material is preferably confined to the core layer(s), the effect on tensile MD stiffness is linear with overall thickness of the core layers. However, bending is not so greatly impacted because the stiffer PLA material of the core layers is preferably located near or at the neutral axis of bending of the multi-layer film while the more compliant, polyolefin containing skin layers are located away from the neutral axis of bending of the multi-layer film. Another advantage to this arrangement is the protection of the notch sensitive PLA material by the tougher and more compliant outer or skin layers.

In some embodiments, a 5 layer multi-layer film has a layer volume fraction ratio of 40 (first outer layer)/5 (first tie layer)/10 (core layer)/5 (second tie layer)/40 (second outer layer)±20%, or 35 (first outer layer)/5 (first tie layer)/20 (core layer)/5 (second tie layer)/35 (second outer layer) ±20%. The multi-layer film may have a MD and CD tensile strength of greater than or equal to 20 MPa but less than 100 MPa, a MD and CD breaking elongation of greater than or equal to 200% but less than 3,000%, and an MD and CD 10% stress of greater than 10 MPa but less than 50 MPa. If the 10% stress is above 50 MPa, then the multi-layer film may become too stiff, harsh, loud, and crinkly, which are not acceptable for some consumer applications.

The polylactic acid may generally be derived from monomer units of any isomer of lactic acid, the monomeric precursor of PLA. Lactic acid can be obtained either by carbohydrate fermentation or by common chemical synthesis. Also known as "milk acid", lactic acid is the simplest hydroxyl acid with an asymmetric carbon atom and two optically active configurations, namely the L and D isomers, which can be produced in bacterial systems, whereas mammalian organisms only produce the L isomer, which is easily assimilated during metabolism.

Lactic acid is mainly prepared by the bacterial fermentation of carbohydrates. These fermentation processes can be classified according to the type of bacteria used. Most fermentation processes use species of Lactobacilli which give high yields of lactic acid. Some organisms predominantly produce the L isomer, such as Lactobacilli amylophilius, *L. bavaricus, L. cosei*, and *L. maltaromicus*, whereas *L. delbrueckii, L. jensenii* or *L. acidophilus* produce the D isomer or a mixture of L and D. In general, the sources of basic sugars are glucose and maltose from corn or potato, sucrose from cane or beet sugar, etc. After separating the lactate solution from the cells (biomass) and other remaining solid materials, the product is then evaporated, crystallized, and acidified to obtain the crude lactic acid. Before undergoing polymerization, it can be purified by separation techniques such as untra-filtration, nano-filtration, electro-dialysis, and ion-exchange processes.

Synthesis of PLA is a multi-step process which can follow at least three main routes. In one production route, lactic acid is condensation polymerized to yield a low molecular weight, brittle polymer which, for the most part, is unusable, unless external coupling agents are employed to increase its chains length. The second route is the azeotropic dehydrative condensation of lactic acid. This can yield high molecular weight PLA without the use of chain extenders or special adjuvents. The third and main process involves the intermediate step of forming lactides from the lactic acid, which are then subjected to ring-opening polymerization (ROP) to obtain high molecular weight PLA.

The polylactic acid may be a homopolymer or a copolymer, such as one that contains monomer units derived from L-lactic acid and monomer units derived from D-lactic acid. Multiple polylactic acids, each having a different ratio between the monomer unit derived from L-lactic acid and the monomer unit derived from D-lactic acid, may be included at any desired percentage.

The physical properties of polylactide are related to the enantiomeric purity of lactic acid stereo-copolymers. The physical properties of polylactide are related to the enantiomeric purity of the lactic acid stereo-copolymers. Homo-PLA is a linear macromolecule with a molecular architecture that is determined by its stereochemical composition. PLA can be produced that is totally amorphous or up to 40% crystalline. PLA resins containing more than 93% of L-lactic acid are semi-crystalline, but PLA having 50 to 93% L-lactic acid is completely amorphous. Thus, the L/D ratio induces or restrains polymer crystallinity.

Both meso- and D-lactides induce twists in the very regular PLLA architecture. Macromolecular imperfections are responsible for the decrease in both the rate and the extent of PLLA crystallization. In practice, most PLAs are made up of L and D,L-lactide copolymers, since the reaction media often contain some meso-lactide impurities. Depending on the preparation conditions, PLLA crystallizes into different forms. The alpha-form exhibits a well-defined diffraction pattern, has a melting temperature of 185° C., and is more stable than its beta-counterpart, which melts at 175° C. The latter can be formed at a high draw ratio and high drawing temperature. The c-form is found by epitaxial crystallization. It has been observed that a blend with equivalent PLLA and PDLA contents gives stereocomplexation (racemic crystallite) of both polymers. This stereocomplex gives mechanical properties higher than those of pure PLLA or PDLA and a high Tm equal to 230° C.

The literature reports different density data for PLA, as crystalline parts can have a density of 1.29 compared to 1.25 for the amorphous material. PLA is a slowly crystallizing polymer similar to PET. As with PET, PLA can be oriented by processing. Chain orientation increases the mechanical strength of PLLA plastics. If orientation is performed at low temperature, the resulting PLLA has enhanced modulus without a significant increase in crystallinity. To determine crystallinity levels by DSC, the value, most often referred in the literature concerning the PLA melt enthalpy at 100% crystallinity, is 93 J/g. Crystallization of the thermally crystallizable but amorphous PLA can be initiated by annealing at temperatures between 75 C and Tm. The annealing of crystallizable PLA copolymers often produces two melting peaks. Different hypothesis have been presented. Some authors found double melting points in PLLA polymers and attributed them to the slow rates of crystallization and recrystallization. The typical Tg of PLA ranges from 50 to 80° C. while the Tm ranges from 130 to 180° C. For instance, enantiomerically pure PLA is a semi-crystalline polymer with a Tg of 55° C. and a Tm of 180° C. For semi-crystalline PLA, the Tm is a function of the different processing parameters and the initial PLA structure. Tm increases with the molecular weight (Mw) until a maximum value. Besides, the crystallinity decreases with increasing Mw. Tg is also determined by the proportion of the different types of lactide. Tm depends on the presence of meso-lactide in the structure which produces a Tm reduction.

PLA can be plasticized using various approaches such as but not exclusive to oligomeric lactic acid (o-LA), citrate ester, or low molecular weight polyethylene glycol (PEG). The effect of plasticization increases the chain mobility and lowers the glass transition temperature to render the PLA less brittle. Other plasticizers may include vitamin based chemistries such as RIKEMAL PL-710 from Riken Vitamin Company.

An example of a suitable polylactic acid polymer that may be used in the present invention is commercially available from Biomer, Inc. of Krailling, Germany, under the name BIOMER (Registered Trademark) L9000. Other suitable polylactic acid polymers are commercially available from Natureworks LLC of Minnetonka, Minn. (NATUREWORKS (Registered trademark)) or Mitsui Chemical (LACEA (Registered Trademark)). Still other suitable polylactic acids may be described in U.S. Pat. Nos. 4,797,468; 5,470,944; 5,770,682; 5,821,327; 5,880,254; and 6,326,458, which are incorporated herein in their entirety by reference thereto for all purposes.

The polylactic acid typically has a number average molecular weight ("Mn") ranging from about 40,000 to about 160,000 grams per mole, in some embodiments from about 50,000 to about 140,000 grams per mole, and in some embodiments, from about 80,000 to about 120,000 grams per mole. Likewise, the polymer also typically has a weight average molecular weight ("Mw") ranging from about 80,000 to about 200,000 grams per mole, in some embodiments from about 100,000 to about 180,000 grams per mole, and in some embodiments, from about 110,000 to about 160,000 grams per mole.

The ratio of the weight average molecular weight to the number average molecular weight ("Mw/Mn"), i.e., the "polydispersity index", is also relatively low. For example, the polydispersity index typically ranges from about 1.0 to about 3.0, in some embodiments from about 1.1 to about 2.0, and in some embodiments, from about 1.2 to about 1.8. The weight and number average molecular weights may be determined by methods known to those skilled in the art.

The polylactic acid may also have an apparent viscosity of from about 50 to about 600 Pascal seconds (Pa·s), in some embodiments from about 100 to about 500 Pa·s, and in some embodiments, from about 200 to about 400 Pa·s, as determined at a temperature of 190 deg. C. and a shear rate of 1000 sec. The melt flow rate of the polylactic acid (on a dry basis) may also range from about 0.1 to about 40 grams per 10 minutes, in some embodiments from about 0.5 to about 20 grams per 10 minutes, and in some embodiments, from about 5 to about 15 grams per 10 minutes, determined at a load of 2160 grams and at 190 deg. C.

Aliphatic biopolymers such as PLA are biodegradable. The main abiotic degradation phenomena involve thermal and hydrolysis degradation. During the composting state, PLA degrades in a multistep process involving different mechanisms. Primarily, after exposure to moisture by abiotic mechanisms, PLA degrades by hydrolysis.

IV. Tie Layers

The multi-layer films comprise one or more tie layers. The tie layers are disposed between the core layer and each of the outer or skin layers. In some embodiments, one or more tie layers are disposed between one of the outer skins and the core layer. In some embodiments, the one or more tie layers are adjacent to or continguous with one of the skin layer and the core layer(s). In some embodiments, the one or more tie layers are adjacent to or continguous with both a skin layer and the core layer. The one or more of the tie layers comprise one or more functionalized polyolefins. In some embodiments, the tie layer comprises from 5%, 10%, 20%, 30%, 40% or 45% to 55%, 60%, 70%, 80%, 90%, or 100% by weight of the tie layer of the one or more functionalized polyolefins. The one or more tie layers can consist essentially of the one or more functionalized polyolefins. The thickness of each tie layer may be between 2.5 vol % and 35 vol % of the total volume of the multi-layer film.

Because of the significant difference in polarity between PLA and polyolefins, blends of these components typically result in incompatible systems with poor physical properties. The multi-layer films therefore incorporate one or more tie layers between the outer layers and the core layer. It has been found that this particular multi-layer structure may provide the MD and/or CD tensile properties useful for products currently made from polyethylene while incorporating a renewable feedstock (PLA). This arrangement also enables downgauging (i.e., thickness reduction or basis weight reduction) due to improvements in stiffness that can be used to further drive sustainability and/or used as a cost savings.

The tie layer may comprise a functionalized polyolefin that possesses a polar component provided by one or more functional groups that is compatible with the PLA of the core layer(s) and a non-polar component provided by an olefin that is compatible with one or more polyolfefins of the outer layer. The polar component may, for example, be provided by one or more functional groups and the non-polar component may be provided by an olefin. The olefin component of the compatibilizer may generally be formed from any linear or branched a-olefin monomer, oligomer, or polymer (including copolymers) derived from an olefin monomer. The a-olefin monomer typically has from 2 to 14 carbon atoms and preferably from 2 to 6 carbon atoms. Examples of suitable monomers include, but not limited to, ethylene, propylene, butene, pentene, hexene, 2-methyl-1-propene, 3-methyl-1-pentene, 4-methyl-1-pentene, and 5-methyl-1-hexene. Examples of polyolefins include both homopolymers and copolymers, i.e., polyethylene, ethylene copolymers such as EPDM, polypropylene, propylene copolymers, and polymethylpentene polymers.

An olefin copolymer can include a minor amount of non-olefinic monomers, such as styrene, vinyl acetate, diene, or acrylic and non-acrylic monomer. Functional groups may be incorporated into the polymer backbone using a variety of known techniques. For example, a monomer containing the functional group may be grafted onto a polyolefin backbone to form a graft copolymer. Such grafting techniques are well known in the art and described, for instance, in U.S. Pat. No. 5,179,164. In other embodiments, the monomer containing the functional groups may be copolymerized with an olefin monomer to form a block or random copolymer. Regardless of the manner in which it is incorporated, the functional group of the compatibilizer may be any group that provides a polar segment to the molecule, such as a carboxyl group, acid anhydride group, acid amide group, imide group, carboxylate group, epoxy group, amino group, isocyanate group, group having oxazoline ring, hydroxyl group, and so forth. Maleic anhydride modified polyolefins are particularly suitable for use in the present invention. Such modified polyolefins are typically formed by grafting maleic anhydride onto a polymeric backbone material. Such maleated polyolefins are available from E. I. du Pont de Nemours and Company under the designation Fusabond, such as the P Series (chemically modified polypropylene), E Series (chemically modified polyethylene), C Series (chemically modified ethylene vinyl acetate), A Series (chemically modified ethylene acrylate copolymers or terpolymers), or N Series (chemically modified ethylene-propylene, ethylene-propylene diene monomer ("EPDM") or ethylene-octene). Alternatively, maleated polyolefins are also available from Chemtura Corp. under the designation Polybond and Eastman Chemical Company under the designation Eastman G series, and AMPLIFY™ GR Functional Polymers (maleic anhydride grafted polyolefins). Other examples include Lotader AX8900 (polyethylene-methyl acrylate-glycidyl methacrylate terpolymer) and Lotader Tex. 8030 (polyethylene-acrylic ester-maleic anhydride terpolymer) available from Arkema.

In some aspects, the tie layer can be a resin composition as disclosed in U.S. Pat. No. 8,114,522, issued Feb. 14, 2012 to Kitora et al. This resin composition includes a modified PO resin and a terpene resin. Alternatively, it includes a polylactic acid resin, a modified polyolefin resin, and a hydrogenated petroleum resin. These compositions are suitable for use as a tie layer between the outer layer and the core layer.

In some embodiments, an outer layer and tie layer may be essentially combined as an outer layer by incorporating a functionalied polyolefin into one or both of the outer layers. In these instances, the multi-layer film may comprise 3 or 4 layers. In the case of a 3 layer film, the film may comprise a first outer layer comprising a polyolefin and/or a functionalized polyolefin, one or more core layers, and a second outer layer comprising a polyolefin and/or a functionalized polyolefin). In the case of a 4 layer film, the film may comprise a first outer layer comprising a polyolefin and/or a functionalized polyolefin, one or more core layers, a tie layer, and a second outer layer comprising a polyolefin.

V. Additives

Any of the layers of the multi-layer film may comprise small amounts of one or more additives. Typically, the additives may comprise less than about 10%, 5%, 4%, 3%, 2%, 1%, 0.5%, 0.1% or 0.01% by weight of the layer of the additive. Some non-limiting examples of classes of additives contemplated include perfumes, dyes, pigments, nanoparticles, antistatic agents, fillers, and combinations thereof. The layers disclosed herein can contain a single additive or a mixture of additives. For example, both a perfume and a colorant (e.g., pigment and/or dye) can be present.

As used herein the term "perfume" is used to indicate any odoriferous material that is subsequently released from the composition as disclosed herein. A wide variety of chemicals are known for perfume uses, including materials such as aldehydes, ketones, alcohols, and esters. More commonly, naturally occurring plant and animal oils and exudates including complex mixtures of various chemical components are known for use as perfumes. The perfumes herein can be relatively simple in their compositions or can include highly sophisticated complex mixtures of natural and/or synthetic chemical components, all chosen to provide the desired scent. Typical perfumes can include, for example, woody/earthy bases containing exotic materials, such as sandalwood, civet and patchouli oil. The perfumes can be of a light floral fragrance (e.g. rose extract, violet extract, and lilac). The perfumes can also be formulated to provide desirable fruity scents, (e.g. lime, lemon, and orange). The perfumes delivered in the compositions and articles of the present invention can be selected for an aromatherapy effect, such as providing a relaxing or invigorating mood. As such, any suitable material that exudes a pleasant or otherwise desirable odor can be used as a perfume active in the compositions and articles of the present invention.

A pigment or dye can be inorganic, organic, or a combination thereof. Specific examples of pigments and dyes contemplated include pigment Yellow (C.I. 14), pigment Red (C.I. 48:3), pigment Blue (C.I. 15:4), pigment Black (C.I. 7), and combinations thereof. Specific contemplated dyes include water soluble ink colorants like direct dyes, acid dyes, base dyes, and various solvent soluble dyes. Examples include, but are not limited to, FD&C Blue 1 (C.I. 42090:2), D&C Red 6(C.I. 15850), D&C Red 7(C.I. 15850:1), D&C Red 9(C.I. 15585:1), D&C Red 21(C.I. 45380:2), D&C Red 22(C.I. 45380:3), D&C Red 27(C.I. 45410:1), D&C Red 28(C.I. 45410:2), D&C Red 30(C.I. 73360), D&C Red 33(C.I. 17200), D&C Red 34(C.I. 15880:1), and FD&C Yellow 5(C.I. 19140:1), FD&C Yellow 6(C.I. 15985:1), FD&C Yellow 10(C.I. 47005:1), D&C Orange 5(C.I. 45370:2), and combinations thereof.

Contemplated fillers include, but are not limited to, inorganic fillers such as, for example, the oxides of magnesium, aluminum, silicon, and titanium. These materials can be added as inexpensive fillers or processing aides. Other inorganic materials that can function as fillers include hydrous magnesium silicate, titanium dioxide, calcium carbonate, clay, chalk, boron nitride, limestone, diatomaceous earth, mica glass quartz, and ceramics. Additionally, inorganic salts, including alkali metal salts, alkaline earth metal salts, phosphate salts, can be used. Additionally, alkyd resins can also be added to the composition. Alkyd resins can comprise a polyol, a polyacid or anhydride, and/or a fatty acid.

Additional contemplated additives include nucleating and clarifying agents for the thermoplastic polymer. Specific examples, suitable for polypropylene, for example, are benzoic acid and derivatives (e.g., sodium benzoate and lithium benzoate), as well as kaolin, talc and zinc glycerolate. Dibenzlidene sorbitol (DBS) is an example of a clarifying agent that can be used. Other nucleating agents that can be used are organocarboxylic acid salts, sodium phosphate and metal salts (e.g., aluminum dibenzoate). In one aspect, the nucleating or clarifying agents can be added in the range from 20 parts per million (20 ppm) to 20,000 ppm, or from 200 ppm to 2000 ppm, or from 1000 ppm to 1500 ppm. The addition of the nucleating agent can be used to improve the tensile and impact properties of the finished composition.

Contemplated surfactants include anionic surfactants, amphoteric surfactants, or a combination of anionic and amphoteric surfactants, and combinations thereof, such as surfactants disclosed, for example, in U.S. Pat. Nos. 3,929,678 and 4,259,217, and in EP 414 549, WO93/08876, and WO93/08874.

Contemplated nanoparticles include metals, metal oxides, allotropes of carbon, clays, organically modified clays, sulfates, nitrides, hydroxides, oxy/hydroxides, particulate water-insoluble polymers, silicates, phosphates and carbonates. Examples include silicon dioxide, carbon black, graphite, grapheme, fullerenes, expanded graphite, carbon nanotubes, talc, calcium carbonate, betonite, montmorillonite, kaolin, zinc glycerolate, silica, aluminosilicates, boron nitride, aluminum nitride, barium sulfate, calcium sulfate, antimony oxide, feldspar, mica, nickel, copper, iron, cobalt, steel, gold, silver, platinum, aluminum, wollastonite, aluminum oxide, zirconium oxide, titanium dioxide, cerium oxide, zinc oxide, magnesium oxide, tin oxide, iron oxides (Fe2O3, Fe3O4) and mixtures thereof. Nanoparticles can increase strength, thermal stability, and/or abrasion resistance of the compositions disclosed herein, and can give the compositions electric properties.

Contemplated anti-static agents include fabric softeners that are known to provide antistatic benefits. These can include those fabric softeners having a fatty acyl group that has an iodine value of greater than 20, such as N,N-di(tallowoyl-oxy-ethyl)-N,N-dimethyl ammonium methylsulfate.

In particular aspects, the filler can comprise renewable fillers. These can include, but are not limited to, lipids (e.g., hydrogenated soybean oil, hydrogenated castor oil), cellulosics (e.g., cotton, wood, hemp, paperboard), lignin, bamboo, straw, grass, kenaf, cellulosic fiber, chitin, chitosan, flax, keratin, algae fillers, natural rubber, nanocrystalline starch, nanocrystalline cellulose, collagen, whey, gluten, and combinations thereof.

VI. Films and Other Articles of Manufacture

Films

The multi-layer films described herein can be processed using conventional procedures for producing films on conventional coextruded film-making equipment. In general, polymers can be melt processed into films using either cast or blown film extrusion methods both of which are described in Plastics Extrusion Technology-2nd Ed., by Allan A. Griff (Van Nostrand Reinhold-1976).

Cast film is extruded through a linear slot die. Generally, the flat web is cooled on a large moving polished metal roll (chill roll) typically impenged with an air knife. It quickly cools, and peels off the first roll, passes over one or more auxiliary rolls, then through a set of rubber-coated pull or "haul-off" rolls, and finally to a winder. In cast embossing, the molten film is passed through a metal roll containing the embossing pattern with a rubber backing roll providing the contact force. The melt is cooled and imparted with the embossing pattern.

In blown film extrusion, the melt is extruded upward through a thin annular die opening. This process is also referred to as tubular film extrusion. Air is introduced through the center of the die to inflate the tube and causes it to expand. A moving bubble is thus formed which is held at constant size by simultaneous control of internal air pressure, extrusion rate, and haul-off speed. The tube of film is cooled by air blown through one or more chill rings surrounding the tube. The tube is next collapsed by drawing it into a flattened frame through a pair of pull rolls and into a winder. Derivatives of the blown film process include double bubble and triple bubble that allow greater orientation.

A coextrusion process requires more than one extruder and either a coextrusion feedblock or a multi-manifold die system or combination of the two to achieve a multilayer film structure. U.S. Pat. Nos. 4,152,387 and 4,197,069, incorporated herein by reference, disclose the feedblock and multi-manifold die principle of coextrusion. Multiple extruders are connected to the feedblock which can employ moveable flow dividers to proportionally change the geometry of each individual flow channel in direct relation to the volume of polymer passing through the flow channels. The flow channels are designed such that, at their point of confluence, the materials flow together at the same velocities and pressure, minimizing interfacial stress and flow instabilities. Once the materials are joined in the feedblock, they flow into a single manifold die as a composite structure. Other examples of feedblock and die systems are disclosed in Extrusion Dies for Plastics and Rubber, W. Michaeli, Hanser, N.Y., 2nd Ed., 1992, hereby incorporated herein by reference. It may be important in such processes that the melt viscosities, normal stress differences, and melt temperatures of the material do not differ too greatly. Otherwise, layer encapsulation or flow instabilities may result in the die leading to poor control of layer thickness distribution and defects from non-planar interfaces (e.g. fish eye) in the multilayer film.

An alternative to feedblock coextrusion is a multi-manifold or vane die as disclosed in U.S. Pat. Nos. 4,152,387, 4,197,069, and 4,533,308, incorporated herein by reference. Whereas in the feedblock system melt streams are brought together outside and prior to entering the die body, in a multi-manifold or vane die each melt stream has its own manifold in the die where the polymers spread independently in their respective manifolds. The melt streams are married near the die exit with each melt stream at full die width. Moveable vanes provide adjustability of the exit of each flow channel in direct proportion to the volume of material flowing through it, allowing the melts to flow together at the same velocity, pressure, and desired width.

Since the melt flow properties and melt temperatures of polymers vary widely, use of a vane die has several advantages. The die lends itself toward thermal isolation characteristics wherein polymers of greatly differing melt temperatures, for example up to 175° F. (80° C.), can be processed together.

Each manifold in a vane die can be designed and tailored to a specific polymer. Thus the flow of each polymer is influenced only by the design of its manifold, and not forces imposed by other polymers. This allows materials with greatly differing melt viscosities to be coextruded into multilayer films. In addition, the vane die also provides the ability to tailor the width of individual manifolds, such that an internal layer can be completely surrounded by the outer layer leaving no exposed edges. The feedblock systems and vane dies can be used to achieve more complex multilayer structures.

The skins, tie-layers, and core can be microlayered using various technologies. In microlayering, the interfacial properties dominate due to the small dimension of the layer thickenesses. Microlayering systems from Nordson/EDI or Cloeren are exemplary processes for completing the microlayering. In preferred embodiments, the skin/tie layer combination are multiplied while the core remains a macrolayer that is not multiplied.

Another means to producing the 5-layer structures of the present invention is through lamination based techniques. The core layer containing the biopolymer may first be oriented and/or printed. The core layer is then coated on both sides with the thick polyolefin rich skins. An aqueous or solvent based adhesive tie layer may be used to attach the various layers during the lamination process. Also, the layers may be adhered using extrusion lamination wherein the lamination adhesive is similar in chemistry to the extrudable tie layers discussed previously. Also, any combination of extrusion and lamination can be used to produce the desired structure.

The films as disclosed herein can be formed into fluid pervious webs suitable for use as a topsheet in an absorbent article. As is described below, the fluid pervious web is desirably formed by macroscopically expanding a film as disclosed herein. The fluid pervious web contains a plurality of macroapertures, microapertures or both. Macroapertures and/or microapertures give the fluid pervious web a consumer-desired fiber-like or cloth-like appearance than webs apertured by methods such as embossing or perforation (e.g. using a roll with a multiplicity of pins) as are known to the art. One of skill in the art will recognize that such methods of providing apertures to a film are also useful for providing apertures to the films as disclosed herein. Although the fluid pervious web is described herein as a topsheet for use in an absorbent article, one having ordinary skill in the art will appreciate these webs have other uses, such as bandages, agricultural coverings, and similar uses where it is desirable to manage fluid flow through a surface.

The macro and microapertures can be formed by applying a high pressure fluid jet comprised of water or the like against one surface of the film, desirably while applying a vacuum adjacent the opposite surface of the film. In general, the film is supported on one surface of a forming structure having opposed surfaces. The forming structure is provided with a multiplicity of apertures there through which place the opposed surfaces in fluid communication with one another. While the forming structure may be stationary or moving, an exemplary execution uses the forming structure as part of a continuous process where the film has a direction of travel and the forming structure carries the film in the direction of travel while supporting the film. The fluid jet and, desirably, the vacuum cooperate to provide a fluid pressure differential across the thickness of the film causing the film to be urged into conformity with the forming structure and to rupture in areas that coincide with the apertures in the forming structure.

The film passes over two forming structures in sequence. The first forming structure has a multiplicity of fine scale apertures which, on exposure to the aforementioned fluid pressure differential, cause formation of microapertures in the web of film. The second forming structure exhibits a macroscopic, three-dimensional cross section defined by a multiplicity of macroscopic cross section apertures. On exposure to a second fluid pressure differential the film substantially conforms to the second forming structure while substantially maintaining the integrity of the fine scale apertures.

Such methods of aperturing are known as "hydroformation" and are described in greater detail in U.S. Pat. Nos. 4,609,518; 4,629,643; 4,637,819; 4,681,793; 4,695,422; 4,778,644; 4,839,216; and 4,846,821.

The apertured web can also be formed by methods such as vacuum formation and using mechanical methods such as punching. Vacuum formation is disclosed in U.S. Pat. No. 4,463,045. Examples of mechanical methods are disclosed in U.S. Pat. Nos. 4,798,604; 4,780,352; and 3,566,726.

Variants of the film described herein are also contemplated. For example, the soft film skin layer disclosed in U.S. Patent Application Ser. No. 61/991,923, "Microtextured Films with Improved Tactile Impression" (P&G Case No. 13349P, filed May 12, 2014), which is herein incorporated by reference, can be substituted for one or more skin layers of the present invention, or can be used in addition to one or more skin layers of the present invention.

Articles

The multi-layer films described herein may be used for a variety of purposes, including but not limited to a packaging material or incorporating in an absorbent article. Some examples of absorbent articles, include, but are not limited to, diapers, training pants, adult incontinence products, pantiliners, tampons, feminine hygiene pads, tissues, and wipes.

In some embodiments, the multi-layer film described herein may be incorporated in an absorbent article comprising a topsheet, a backsheet, and an absorbent core positioned at least partially between or intermediate the topsheet and the backsheet. The multi-layer films described herein may be used to form at least a portion of the topsheet and/or the backsheet. At least a portion of the topsheet may be liquid permeable while the backsheet is liquid impermeable, or at least substantially liquid impermeable. The topsheet is the part of the absorbent article that is directly in contact with the wear's skin. The topsheet may be joined to the backsheet, the core and/or any other layers as is known in the art. Usually, the topsheet and the backsheet are joined directly to each other in some locations (e.g., on or close to the periphery of the article) and are indirectly joined together in other locations by directly joining them to one or more other elements of the absorbent article. The backsheet is generally that portion of the absorbent article positioned adjacent the garment-facing surface of the absorbent core and which prevents, or at least inhibits, the exudates aabsorbed and contained therein from soiling articles such as bedsheets and undergarments. Some examples of absorbent articles are described in USPNs 2015/0065981; 3,860,003; 5,221,274; 5,554,145; 5,569,234; 5,580,411 and 6,004,306.

VIII. Methods

Layer Thickness and Caliper Volume

The overall thickness of the multi-layer film may be measured using the methodology set forth in ISO 4593: 1993, Plastics-Film and sheeting-Determination of thickness by mechanical scanning.

Layer thickness may be either estimated or measured. For estimation, the feed rate of each extruder is controlled through mass rate feedback. From the solid phase density for each layer, the input extruder mass federate can be converted to a volumetric feed rate for each layers, which is used to determine input layer ratio. This calculation is valid as long as the layers produce a uniform thickness upon extrusion.

Alternatively, thickness can be directly measured using optical means. The film is first mounted into a special fixture that restricts the movement of the film and enables a very thin slice of material in the CD to be obtained. The slit is implemented using a microtome blade and liquid nitrogen to cool the sample. After cutting, the sample is mounted onto the stage of an optical microscope. The microscope is operated with ~70% transmitted light through the sample and 30% reflected light. The image of the layers is captured using Motic software, which has been calibrated using a measurement standard. The thickness of each layer is calculated from the Motic software calibration.

Mechanical Properties

Break stress, 10% stress and extensibility are measured according to ASTM method D882, Standard Test Method for Tensile Properties of Thin Plastic Sheeting. Tensile testing may be done using an MTS Systems Corporation Synergie 400 instrument with a 100N load cell or an equivalent tensile testing machine. For the Examples, test samples were pulled according to ASTM D882 with a crosshead speed of 25.4 cm/min and a gage length of 5 cm. Tensile at break and 2% secant modulus were recorded and reported in SI units. Mechanical properties of the multi-layer films, including ultimate tensile strength, elongation at break, and 10% elongational stress, may be quantified using the standard tensile testing method described above. In some embodiments, particularly in the MD direction, the multi-layer films may have a break stress of at least 20 Mpa, 10% stress of at least 10 MPa, and extensibility of at least 200%. In the CD direction, the multi-layer films may have a break stress of at least 20 MPa, 10% stress of at least 10 MPa, and extensibility of at least 200%.

VIII. Examples

The following examples further describe and demonstrate particular executions within the scope of the present invention. The examples are given solely for the purpose of illustration and are not to be construed as limitations of the present invention since many variations thereof are possible without departing from the spirit and scope of the invention. Ingredients are identified by chemical name, or otherwise defined below.

TABLE 1

| Example | PLA content (wt %/vol %) | MD | | | CD | | |
|---|---|---|---|---|---|---|---|
| | | Break Stress (Mpa) | 10% Stress (MPa) | Extensibility | Break Stress (MPa) | 10% Stress (MPa) | Extensibility |
| Desired | >10 wt % | >20 | >10 | >200% | >20 | >10 | >200% |
| Targets | | <100 | <50 | <3,000% | <100 | <50 | <3,000% |
| Comparative Example #1 | 100%/100% | 87.3 | 32.6 | 12% | 37.4 | 0.1 | 4% |
| Comparative Example #2 | 0%/0% | 36.6 | 8.6 | 865% | 33.4 | 11.1 | 792% |
| Comparative Example #3 | 0%/0% | 50.3 | 12.1 | 743% | 43.5 | 13.3 | 806% |
| Example #1 | 13%/10% | 37.6 | 14.5 | 662% | 35.0 | 14.1 | 761% |
| Example #2 | 25%/20% | 29.2 | 21.8 | 247% | 22.8 | 19.8 | 436% |
| Example #3 | 22%/20% | 40.0 | 11.9 | 648% | 26.3 | 11.0 | 646% |
| Example #4 | 23%/20% | 23.0 | 16.9 | 248% | 25.1 | 11.7 | 714% |

Comparative Example #1 containing 100 wt % Nature Works 4042D is prepared on a 1 inch Merritt Davis extruder with a 24 L:D. The raw materials (typically in pellet form) are introduced into the hopper as a physically mixed blend. The materials are melt mixed and pumped by the extruder to the downstream film die. The extruder was attached to a 25 cm EDI coat hanger die with a no pressure lip setting of 750 microns. The resulting extrudate was cast onto a chrome finish chill roll operating at 30 Celsius over a 4" melt curtain. The extrudate was cooled to produce the final film form that was wrapped continuously onto a 75 mm core.

Comparative example #2 and #3 and Examples 1-4 are prepared in accordance with the following: A Dr. Collin BL 180/400 blown film line is used to produce the film. The die diameter is 60 mm with a die gap of 1.5 mm. The die temperature is set based upon the material being extruded through each pancake.

For comparative example #2: The following extruder combination was used: Three single screw extruders are connected to a 3-layer pancake die. Extruder A feeding the interior skin is a 25 mm screw with a Maddock tip. Extruder B feeding the core layer is a 30 mm screw with a Maddock tip. Extruder C feeding the exterior skin layer is a 30 mm screw with a Maddock tip.

Comparative example #3 and the examples 1-4 are prepared in accordance with the following: Five single screw extruders are connected to a 5-layer pancake die. Extruder A feeding the interior skin is a 30 mm screw with a Maddock tip. Extruder B feeding the tie layer closest to the interior skin is a 20 mm GP screw. Extruder C feeding the core layer is a 30 mm extruder with a Maddock tip. Extruder D feeding the tie layer closest to the exterior skin is a 20 mm GP screw. Extruder E feeding the exterior skin layer is a 25 mm screw with a Maddock tip.

For all films produced, the nominal throughput through the die is set around 15 kg/hr (each extruder adjusted to provide the targeted layer ratio). The line speed is adjusted typically between 10 and 30 m/min to achieve a targeted film thickness of 50 micron. The blow-up-ratio (BUR) is kept constant between 2.2 and 2.4. Air flow is set between 50 and 100% using the Dr. Collin BL 180/400 high speed blower setting. Film is collected onto a 75 mm winding cone and allowed to age for one day before mechanical testing.

Formulation Information:

Comparative Example #2: 100% Dowlex 2045G is loaded into the hopper of Extruders A, B, and C. The extruder output is adjusted such that A and C each supply 20 vol % of the total feed rate of ~15 kg/hr. The extruder output of B is adjusted to achieve the remaining 60 vol %. The zone temperatures in the extruders are set such that an exit melt temperature of ~230 C is achieved for each extruder. The line is operated at ~13 m/min to achieve a targeted 50 micron film at a 2.2 BUR. The die temperature and associated pancakes are all set to 230 C.

Comparative Example #3: 70% Dowlex 2045G and 30% Dowlex 2027 is loaded into the hopper of Extruders A, B, C, D, and E. The extruder output is adjusted such that A, B, D, and E each supply 10 vol % of the total feed rate of ~15 kg/hr. The extruder output of B is adjusted to achieve the remaining 60 vol %. The zone temperatures in the extruders are set such that an exit melt temperature of ~230 C is achieved for each extruder. The line is operated at ~13 m/min to achieve a targeted 50 micron film at a 2.2 BUR. The die temperature and associated pancakes are all set to 230 C.

Example #1: 94.5 wt % Dowlex 2045G and 5.5 wt % Ampacet 110359-C is loaded into the hopper of skin Extruders A and E. The output of extruders A and E are set to produce volume ratios of 40% for each skin for a total of 80 vol % skins. The temperatures are set such that the melt temperature exits at around 220 C. Extruders B and D are loaded with 100% Mitsui SF600 and the output is set such that each tie layer extruder produces 5 vol % and the exit melt temps are 200 C. Extruder C is loaded with 99 wt % NatureWorks 4042D and 1 wt % Clarient CESA Extend # with an extruder output necessary to produce 10 vol % in the core and an exit melt temperature of 190 C. The extruder output is adjusted such that ~15 kg/hr. The line is operated at ~13 m/min to achieve a targeted 50 micron film at a 2.2 BUR. The die and all five pancakes are operated at 200 C.

Example #2: 93.5 wt % Dowlex 2045G and 6.5 wt % Ampacet 110359-C is loaded into the hopper of skin Extruders A and E. The output of extruders A and E are set to produce volume ratios of 35% for each skin for a total of 70 vol % skins. The temperatures are set such that the melt temperature exits at around 220 C. Extruders B and D are loaded with 100% Mitsui SF600 and the output is set such that each tie layer extruder produces 5 vol % and the exit melt temps are 200 C. Extruder C is loaded with 99 wt % NatureWorks 4042D and 1 wt % Clarient CESA Extend # with an extruder output necessary to produce 20 vol % in the core and an exit melt temperature of 190 C. The extruder output is adjusted such that ~15 kg/hr. The line is operated at ~13 m/min to achieve a targeted 50 micron film at a 2.2 BUR. The die and all five pancakes are operated at 200 C.

Example #3 (3B5-9): 93.0 wt % Dowlex 2045G and 7.0 wt % Ampacet 110359-C is loaded into the hopper of skin Extruders A and E. The output of extruders A and E are set to produce volume ratios of 35% for each skin for a total of 70 vol % skins. The temperatures are set such that the melt temperature exits at around 220 C. Extruders B and D are loaded with 100% Mitsui SF600 and the output is set such that each tie layer extruder produces 5 vol % and the exit melt temps are 200 C. Extruder C is loaded with 89 wt % NatureWorks 4043D, 10 wt % Riken PL-012, and 1 wt % Clarient CESA Extend with an extruder output necessary to produce 20 vol % in the core and an exit melt temperature of 190 C. The extruder output is adjusted such that ~15 kg/hr. The line is operated at ~13 m/min to achieve a targeted 50 micron film at a 2.2 BUR. The die and all five pancakes are operated at 200 C.

Example #4 (3B5-12): 93.5 wt % Dowlex 2045G and 6.5 wt % Ampacet 110359-C is loaded into the hopper of skin Extruders A and E. The output of extruders A and E are set to produce volume ratios of 35% for each skin for a total of 70 vol % skins. The temperatures are set such that the melt temperature exits at around 220 C. Extruders B and D are loaded with 50 wt % Mitsui SF600 and 50 wt % NatureWorks 4043D and the output is set such that each tie layer extruder produces 10 vol % and the exit melt temps are 200 C. Extruder C is loaded with 99 wt % NatureWorks 4043D and 1 wt % Clarient CESA Extend # with an extruder output necessary to produce 10 vol % in the core and an exit melt temperature of 190 C. The extruder output is adjusted such that ~15 kg/hr. The line is operated at ~13 m/min to achieve a targeted 50 micron film at a 2.2 BUR. The die and all five pancakes are operated at 200 C.

As shown in Table 1, compositions comprising 12%-25 wt % PLA as a thin core layer produced films having PO-like film characteristics. Of note is that extensibility dropped in both the MD and the CD directions as the PLA level increased but was still acceptable up to about 25 wt % PLA as a thin core layer. The improvements in 10% stress while maintaining acceptable values in the other key measures allows the film to be downgauged (thickness reduced), which can further drive sustainability and/or cost savings. Net, the films of the present invention allow acceptable performance while enabling both increased sustainability and potential downgauging in applications requiring higher stiffness.

The extent of layer adhesion can be controlled by varying the amount and chemistry of the tie layers. The tie layers can even be removed to enable a film that easily delaminates (essentially a 3-layer coextrusion wherein the core layer comprises greater than 95 wt % by weight of the core composition of PLA).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited in the Detailed Description are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A multi-layered film comprising at least 5 layers and having a total thickness from about 10 microns to about 100 microns, wherein the film comprises:
    (a) a first outer layer comprising from about 75% to about 100%, by weight of the first layer, of one or more polyolefins;
    (b) a first tie layer comprising from about 5% to about 100%, by weight of the first tie layer, of one or more functionalized polyolefins;
    (c) a core layer comprising from about 75% to about 100%, by weight of the core layer, of polylactic acid, wherein the multi-layer film has a total volume and the core layer comprises from about 5% to about 30% of the total volume of the film;
    (d) a second tie layer comprising from about 5% to about 100%, by weight of second tie layer, of one or more functionalized polyolefins; and
    (e) a second outer layer comprising from about 75% to about 100%, by weight of the second outer layer, of one or more polyolefins;
    wherein the first tie layer is disposed between the first outer layer and the core layer, and wherein the second tie layer is disposed between the core layer and the second outer layer.

2. The multi-layered film according to claim 1, wherein the first and second tie layers consist essentially of the one or more functionalized polyolefins.

3. The multi-layered film according to claim 1, wherein the one or more polyolefins of the first outer layer comprises a polyethylene or a blend of polyethylenes, and wherein the polyethylene or the blend of polyethylenes has an average density of about 0.85 g/cm$^3$ to about 0.93 g/cm$^3$.

4. The multi-layered film according to claim 1, wherein the one or more polyolefins of the second outer layer comprises a polyethylene or a blend of polyethylenes, and wherein the polyethylene or the blend of polyethylenes has an average density of about 0.85 g/cm$^3$ to about 0.93 g/cm$^3$.

5. The multi-layered film according to claim 1, wherein the multi-layered film comprises tensile properties of:
    (a) Break Stress according to ASTM D882 from about 20 MPa to about 100 MPa; and/or
    (b) 10% Stress according to ASTM D882 from about 10 MPa to about 50 MPa; and/or
    (c) Extensibility according to ASTM D882 from about 200% to about 900%.

6. The multi-layered film according to claim 1, wherein the first outer layer or the second outer layer comprises from about 1% to about 25%, by weight of the first outer layer or the second outer layer, of at least one thermoplastic polymer derived from renewable resources, according to ASTM D6866 test method B.

7. A packaging material comprising the multi-layer film according to claim 1.

8. A package comprising the multi-layer film according to claim 6.

9. A multi-layered film comprising at least 3 layers and having a total thickness from about 10 microns to about 100 microns, wherein the film comprises:
    (a) a first outer layer, comprising from about 75% to about 100%, by weight of the first outer layer, of one or more polyolefins;
    (b) a core layer comprising from about 95% to about 100%, by weight of the core layer, of polylactic acid, wherein the multi-layer film has a total volume and the core layer comprises from 5% to 30% of the total volume of the multi-layer film; and
    (c) a second outer layer comprising from about 75% to about 100%, by weight of the second outer layer, of one or more polyolefins; and
    wherein the core layer is disposed between the first outer layer and the second outer layer.

10. The multi-layered film according to claim 9, wherein first outer layer or the second outer layer comprise at least about 20%, by weight of the first outer layer or the second outer layer, of a functionalized polyolefin.

11. The multi-layered film according to claim 9, wherein the first outer layer or the second outer layer comprises from about 1% to about 25%, by weight of the first outer layer or the second outer layer, of at least one thermoplastic polymer derived from renewable resources, according to ASTM D6866 test method B.

12. A packaging material comprising the multi-layer film according to claim 9.

13. A packaging material comprising the multi-layer film according to claim 11.

14. A multi-layered film comprising at least 4 layers and having a total thickness from about 10 microns to about 100 microns, wherein the film comprises:
    (a) a first outer layer comprising from about 75% to about 100%, by weight of the first outer layer, of one or more polyolefins;
    (b) a first tie layer comprising from about 5% to about 100%, by weight of the first tie layer, of one or more functionalized polyolefins;
    (c) a core layer comprising from about 95% to about 100%, by weight of the core layer, of polylactic acid, wherein the multi-layer film has a total volume and the core layer comprises from about 5% to about 30% of the total volume of the multi-layer film; and
    (d) a second outer layer comprising from 75% to 100%, by weight of the second outer layer, of one or more polyolefins; and
    wherein the core layer is disposed between the first outer layer and the second outer layer.

15. The multi-layered film according to claim 14, wherein the second outer layer comprise at least about 20%, by weight of the second outer layer, of a functionalized polyolefin.

16. The multi-layered film according to claim 14, wherein the first outer layer or the second outer layer comprises from about 1% to about 25%, by weight of the first outer layer or the second outer layer, of at least one thermoplastic polymer derived from renewable resources, according to ASTM D6866 test method B.

17. A packaging material comprising the multi-layer film according to claim 14.

18. A renewable packaging material comprising the multi-layer film according to claim 16.

19. A multi-layered film comprising at least 5 layers and having a total thickness from about 10 microns to about 100 microns, wherein the film comprises:
- (a) a first outer layer comprising one or more biodegradable thermoplastic polymers;
- (b) a first tie layer comprising from about 5% to about 100%, by weight of the first tie layer, of one or more functionalized polyolefins;
- (c) a core layer comprising from about 75% to about 100%, by weight of the core layer, of polylactic acid, wherein the multi-layer film has a total volume and the core layer comprises from about 5% to about 30% of the total volume of the film;
- (d) a second tie layer comprising from about 5% to about 100%, by weight of second tie layer, of one or more functionalized polyolefins; and
- (e) a second outer layer comprising one or more biodegradable thermoplastic polymers; and
  wherein the first tie layer is disposed between the first outer layer and the core layer, and wherein the second tie layer is disposed between the core layer and the second outer layer.

20. The multi-layered film according to claim 19, wherein the multi-layered film comprises tensile properties of:
- (a) Break Stress according to ASTM D882 from about 20 MPa to about 100 MPa; and
- (b) 10% Stress according to ASTM D882 from about 10 MPa to about 50 MPa; and
- (c) Extensibility according to ASTM D882 from about 200% to about 900%.

* * * * *